US011618927B2

(12) United States Patent
Magliocco et al.

(10) Patent No.: US 11,618,927 B2

(45) Date of Patent: Apr. 4, 2023

(54) METHOD OF DISTINGUISHING UROTHELIAL CARCINOMA FROM LUNG AND HEAD AND NECK SQUAMOUS CELL CARCINOMA

(71) Applicant: H. Lee Moffitt Cancer Center and Research Institute, Inc., Tampa, FL (US)

(72) Inventors: Anthony M. Magliocco, Orlando, FL (US); Soner Altiok, Tampa, FL (US); Jasreman Dhillon, Tampa, FL (US); Yin Xiong, Tampa, FL (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 441 days.

(21) Appl. No.: 16/800,280

(22) Filed: Feb. 25, 2020

(65) Prior Publication Data

US 2020/0190603 A1 Jun. 18, 2020

Related U.S. Application Data

(63) Continuation of application No. PCT/US2018/056864, filed on Oct. 22, 2018.

(60) Provisional application No. 62/574,998, filed on Oct. 20, 2017.

(51) Int. Cl.

| | |
|---|---|
| ***C12Q 1/6886*** | (2018.01) |
| ***A61K 33/243*** | (2019.01) |

(52) U.S. Cl.

CPC .......... *C12Q 1/6886* (2013.01); *A61K 33/243* (2019.01); *C12Q 2600/158* (2013.01)

(58) Field of Classification Search

CPC .................................................... C12Q 1/6886

See application file for complete search history.

(56) References Cited

U.S. PATENT DOCUMENTS

| | | | |
|---|---|---|---|
| 2013/0172203 | A1 | 7/2013 | Yeatman et al. |
| 2014/0349856 | A1 | 11/2014 | Schnabel et al. |
| 2015/0293098 | A1 | 10/2015 | Hayes |

OTHER PUBLICATIONS

International Search Report and Written Opinion issued by the International Searching Authority dated Feb. 6, 2019 for corresponding international patent application No. PCT/US18/56864.

Warth et al. Loss of aquaporin-4 expression and putative in a non-small cell lung cancer. BMC Cancer, May 6, 2011, vol. 11, p. 161 (pp. 1-9). Especially p. 4, Table 2.

Yafi et al. First- and second-line therapy for metastatic urothelial carcinoma of the bladder. Current Oncology, Feb. 2011, vol. 18, No. 1, e25-34. Entire document, especially abstract.

International Preliminary Report on Patentability issued by the International Bureau on Apr. 30, 2020 for corresponding International patent application No. PCT/US18/56864.

*Primary Examiner* — Kevin E Weddington

(74) *Attorney, Agent, or Firm* — Michele L. Lawson; Smith & Hopen, P.A.

(57) ABSTRACT

A method of distinguishing between urothelial carcinoma and squamous cell carcinoma of head and neck and lung primaries is presented. A 19-gene signature was developed which differentiates between metastatic urothelial carcinoma and squamous cell carcinoma in a metastatic site when the primary site is either known or unknown.

10 Claims, 6 Drawing Sheets

| data source | # samples | actual type | classified type | | accuracy |
|---|---|---|---|---|---|
| | | | urothelial | lung, head & neck | |
| TCC | 161 | urothelial | 157 | 4 | 97.52% |
| TCC | 306 | SCC lung + HN | 4 | 302 | 98.69% |
| GEO | 96 | SCC HN | 0 | 96 | 100.00% |
| GEO | 93 | urothelial | 93 | 0 | 100.00% |
| GEO | 18 | SCC Lung | 2 | 16 | 88.89% |

Figure 1

| Gene Symbol |
| --- |
| AQP4 |
| ATP13A4 |
| C4BPA |
| CAMK2N1 |
| FMO2 |
| FOXE1 |
| GATA3 |
| HOXA11 |
| IRX2 |
| LRRC4 |
| NAPSA |
| PEBP4 |
| RPL39L |
| SCGB3A1 |
| SCGB3A2 |
| SFTA1P |
| SFTPA2 |
| SFTPB |
| SFTPD |

Figure 3

| gene symbol | mean for lung+HN | mean for urothelial | urothelial up/down | p | Bonferroni adjusted p-value |
|---|---|---|---|---|---|
| AQP4 | 5.11193 | 2.68887 | down | 3.29E-58 | 8.67E-54 |
| ATP13A4 | 5.64800 | 3.04071 | down | 8.76E-63 | 2.31E-58 |
| C4BPA | 8.18984 | 3.54031 | down | 2.80E-70 | 7.38E-66 |
| CAMK2N1 | 6.91974 | 9.14608 | up | 1.27E-61 | 3.35E-57 |
| FMO2 | 7.09095 | 4.00593 | down | 2.99E-62 | 7.88E-58 |
| FOXE1 | 5.77846 | 3.67885 | down | 1.99E-62 | 5.24E-58 |
| GATA3 | 6.50908 | 10.20573 | up | 5.12E-58 | 1.35E-53 |
| HOXA11 | 4.24282 | 6.51236 | up | 3.29E-59 | 8.67E-55 |
| IRX2 | 7.92348 | 3.55929 | down | 5.20E-86 | 1.37E-81 |
| LRRC4 | 7.14153 | 4.93293 | down | 8.80E-55 | 2.32E-50 |
| NAPSA | 8.10169 | 4.06883 | down | 1.75E-71 | 4.61E-67 |
| PEBP4 | 6.31440 | 3.28602 | down | 1.23E-54 | 3.24E-50 |
| RPL39L | 9.51187 | 6.44351 | down | 3.12E-57 | 8.22E-53 |
| SCGB3A1 | 7.71386 | 4.43185 | down | 1.65E-55 | 4.35E-51 |
| SCGB3A2 | 8.97742 | 3.20569 | down | 2.93E-88 | 7.72E-84 |
| SFTA1P | 5.61759 | 3.04311 | down | 1.62E-66 | 4.27E-62 |
| SFTPA2 | 9.91195 | 4.06143 | down | 5.09E-73 | 1.34E-68 |
| SFTPB | 8.17966 | 3.93049 | down | 8.08E-89 | 2.13E-84 |
| SFTPD | 8.99277 | 4.42849 | down | 6.02E-78 | 1.59E-73 |

Figure 6

METHOD OF DISTINGUISHING UROTHELIAL CARCINOMA FROM LUNG AND HEAD AND NECK SQUAMOUS CELL CARCINOMA

CROSS REFERENCE TO RELATED APPLICATIONS

This is a continuation of and claims priority to International Patent Application No. PCT/US2018/056864, filed Oct. 22, 2018, which claims priority to U.S. Provisional Patent Application No. 62/574,998, entitled "A Method of Distinguishing Urothelial Carcinoma from Lung and Head and Neck Squamous Cell Carcinoma", filed on Oct. 20, 2017, the contents of which are herein incorporated by reference.

FIELD OF INVENTION

This invention relates to tumorigenic assays. Specifically, the invention provides a method of distinguishing between urothelial carcinoma and head and neck (H&N) and lung squamous cell carcinoma using a 19-gene signature.

BACKGROUND OF THE INVENTION

An estimated 75,534 urothelial cancer cases were diagnosed in 2016 of which approximately 15% resulted in metastasis. Urothelial carcinoma (UC) can mimic a squamous cell carcinoma (SCC) of the lung and head and neck. Determining whether a solitary lung nodule is primary lung squamous cell cancer or metastatic urothelial cancer (UC) is difficult particularly in a patient with history of invasive urothelial cancer. Presently there is no current standard to distinguish between UCs and SCCs (Head & Neck or lung) for proper patient management. The distinction is currently based on histological appearance, however, given their morphologic similarities, UCs and SCCs of lung or head and neck cannot be distinguished in most cases. Further, these two cancers have an overlapping immunohistochemical profile (both positive for CK5/6, p63 and p40). GATA3 although relatively specific for UC, can also be expressed in SCC.

In the lungs, it is important to distinguish a primary Squamous Cell Carcinoma from metastatic Urothelial Carcinoma (transitional cell carcinoma) and assign the correct stage, since their treatment and prognosis are different. The treatment of a primary localized lung lesion is surgery whereas a metastatic lesion to the lung would require systemic therapy such as chemo or immunotherapy. Similarly, for metastases from unknown primary it is important to distinguish a squamous cell carcinoma from a urothelial carcinoma especially in poorly differentiated cases where the immunoprofile many times is overlapping.

Given the shortcomings of the currently used methods, what is needed is a method of accurately distinguishing between urothelial carcinoma and squamous cell carcinoma of the lung and head and neck.

SUMMARY OF INVENTION

The inventors have used gene expression profiling to compare SCC and UC in identifying a specific number of differentially expressed genes, which ultimately can prove practical in distinguishing metastatic SCC from UC. The Principal Component Analysis (PCA) has shown high accuracy in classifying patients with SCC and UC with 19 genes.

Biomarkers, methods, assays, and kits are provided for diagnosing patients with urothelial carcinoma or squamous cell carcinoma of the head and neck (H&N) or lung. The method can therefore also be used to select the appropriate treatment for a subject diagnosed with urothelial carcinoma or squamous cell carcinoma of the H&N or lung. In particular, the assays and kits can contain primers, probes, or binding agents for detecting expression of at least 2, 3, 4, 5, 6, 7, 8, 9, 10, 11, 12, 13, 14, 15, 16, 17, 18, or 19 genes selected from the group consisting of AQP4, ATP13A4, C4BPA, CAMK2N1, FMO2, FOXE1, GATA3. HOXA11, IRX2, LRRC4, NAPSA, PEBP4, RPL39L, SCGB3A1, SCGB3A2, SFTA1P, SFTPA2, SFTPB, and SFTPD.

The disclosed method can involve obtaining a biological sample (e.g., biopsy) from the subject and determining levels of at least 2, 3, 4, 5, 6, 7, 8, 9, 10, 11, 12, 13, 14, 15, 16, 17, 18, or 19 of the disclosed genes in the biological sample. In some embodiments, the method involves comparing the gene expression levels to control values to produce a gene profile. The method can then comprise calculating a risk score from the gene profile.

In an embodiment, a method of diagnosing between urothelial carcinoma (UC) and squamous cell carcinoma (SCC) in a patient and treating the patient according to the diagnosis is presented comprising: obtaining a tumor sample from the patient; obtaining expression levels of two or more genes in the tumor sample selected from the group consisting of AQP4, ATP13A4, C4BPA, CAMK2N1, FMO2, FOXE1, GATA3 HOXA11, IRX2, LRRC4, NAPSA, PEBP4, RPL39L, SCGB3A1, SCGB3A2, SFTA1P, SFTPA2, SFTPB, and SFTPD; performing Principal Component Analysis (PCA) on the expression levels of the at least two or more genes to obtain a first Principal Component Analysis score (PCA1) and a second Principal Component Analysis score (PCA2) wherein a diagnosis of UC is given if the PCA1 is below −5.1036 and the PCA2 is below 2.147621 or a diagnosis of SCC is given if the PCA1 is above −5.1036 and the PCA2 is above 2.147621; and treating the patient using surgery if the diagnosis is SCC or treating the patient by administering chemotherapy or immunotherapy if the diagnosis is UC.

The tumor sample can be taken from a lung, including a lung nodule, or taken from any metastatic site even if the primary site is unknown. In some embodiments, the patient may currently have or previously had urothelial carcinoma.

The SCC can be a carcinoma of head and neck or lung primaries. The UC can be metastatic.

If the diagnosis is UC and chemotherapy is administered, it can be a therapeutically effective amount of a platinum-based chemotherapeutic agent such as cisplatin.

The expression levels of the two or more genes can be measured using multiplex PCR or HuRSTA chips.

In some embodiments, the expression levels of all the genes AQP4, ATP13A4, C4BPA, CAMK2N1, FMO2, FOXE1, GATA3, HOXA11, IRX2, LRRC4, NAPSA, PEBP4, RPL39L, SCGB3A1, SCGB3A2, SFTA1P, SFTPA2, SFTPB, and SFTPD are measured.

In an embodiment, a method of diagnosing and treating metastases from unknown primary in a patient is presented comprising: obtaining a tumor sample from a metastatic site in the patient; measuring expression levels of genes AQP4, ATP13A4, C4BPA, CAMK2N1, FMO2, FOXE1, GATA3, HOXA11, IRX2, LRRC4, NAPS A, PEBP4, RPL39L, SCGB3A1 SCGB3A2 SFTA1P, SFTPA2, SFTPB, and SFTPD in the tumor sample; performing Principal Component Analysis (PCA) on the expression levels of the at least two or more genes to obtain a first Principal Component Analysis score (PCA1) and a second Principal Component Analysis score (PCA2) wherein a diagnosis of UC is given if the PCA1 is below −5.1036 and the PCA2 is below 2.147621 and a diagnosis of SCC is given if the PCA1 is above −5.1036 and the PCA2 is above 2.147621; and treating the patient using surgery if the diagnosis is SCC or treating the patient by administering chemotherapy or immunotherapy if the diagnosis is UC.

The metastatic site can be a lung. If the diagnosis is UC and chemotherapy is administered, it can be a therapeutically effective amount of a platinum-based chemotherapeutic agent such as cisplatin. The expression levels of the two or more genes can be measured using multiplex PCR or HuRSTA chips.

BRIEF DESCRIPTION OF THE DRAWINGS

For a fuller understanding of the invention, reference should be made to the following detailed description, taken in connection with the accompanying drawings, in which:

FIG. 1 is a table depicting the accuracy for each of the five datasets at the optimal cutoffs of first principal component (PCA1) and second principal component (PCA2) for the 19-gene signature.

FIG. 3 is a table depicting the 19-gene signature.

FIG. 6 is a table depicting the differential gene expression for the 19 genes in the signature.

DETAILED DESCRIPTION OF THE PREFERRED EMBODIMENT

Figure 2:
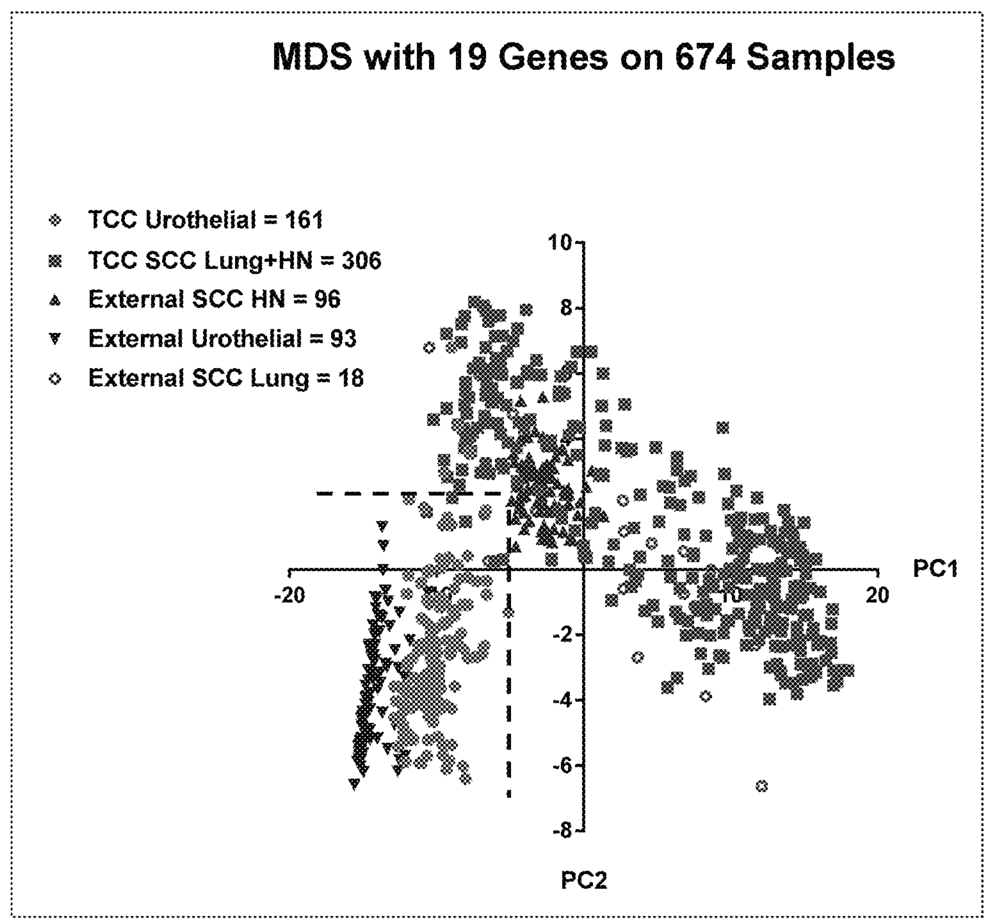
FIG. 2 is a scatterplot depicting PCA1 and PCA2 of the 19 genes for the 674 squamous cell carcinoma cases. The dashed lines are specified by the cutoff (PC1<−5.1036 and PC2<2.1476) and serve as the borderlines to delimit the area for urothelial cancer samples. The green dots represent the 161 TCC urothelial samples, all but 4 of which fall within the area defined by the dashed lines. The blue triangles represent the 93 urothelial samples from the external dataset (GSE31684), all of which fall within the urothelial area. The red squares represent the 306 TCC SCC lung and head-and-neck samples, all but 4 of which are outside of the urothelial area. The purple circles represent the 18 SCC lung cancer samples from the external dataset (GSE10245), all but 2 of which are outside of the urothelial area. The dark red triangles represent the 96 SCC head-and-neck samples from the external dataset (GSE31056), all of which are outside of the urothelial area.
Figure 4:
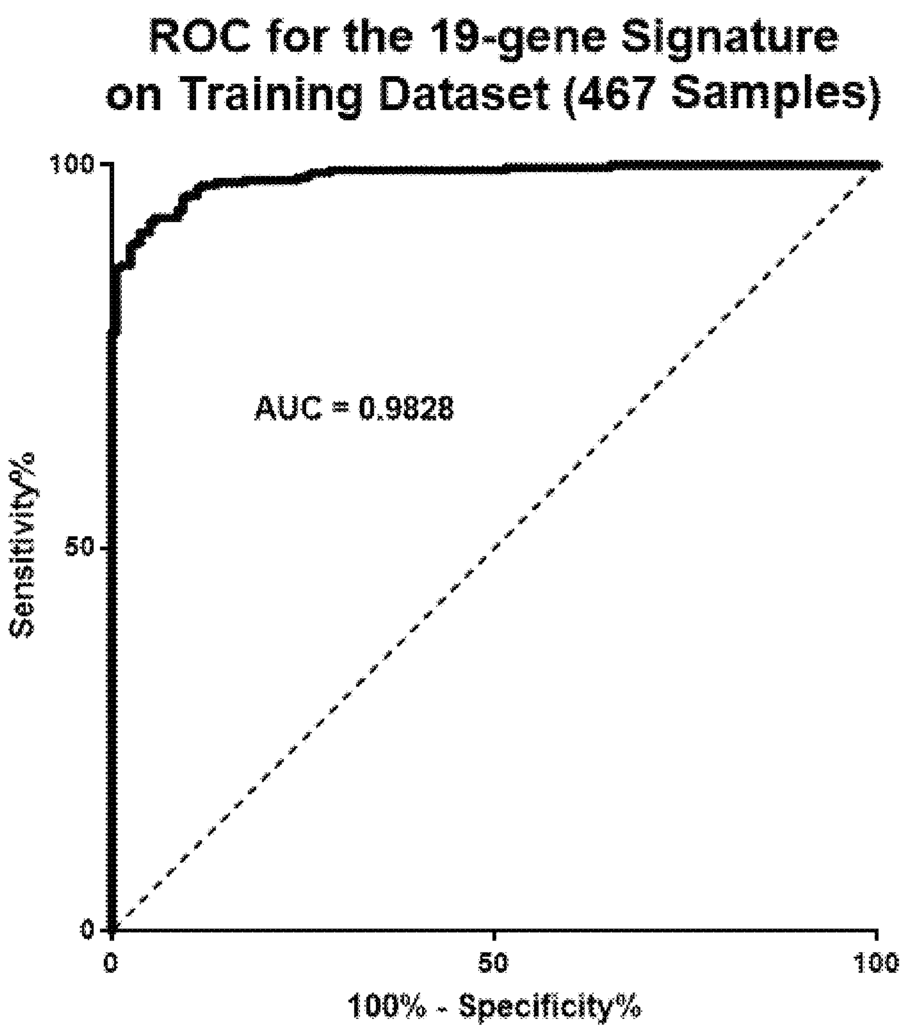
FIG. 4 is a graph depicting the ROC for the 19-gene signature on the training dataset (467 samples).
Figure 5:
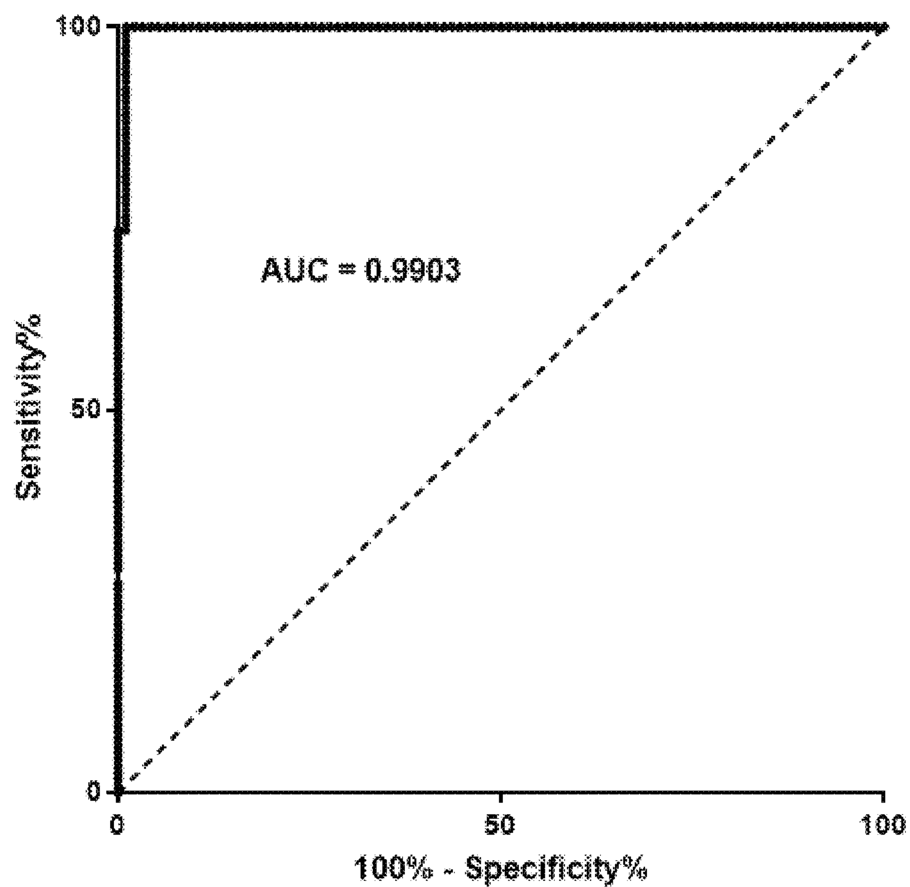
FIG. 5 is a graph depicting the ROC for the 19-gene signature on the validation dataset (207 samples).

In the following detailed description of the preferred embodiments, reference is made to the accompanying drawings, which form a part hereof, and within which are shown by way of illustration specific embodiments by which the invention may be practiced. It is to be understood that other embodiments may be utilized, and structural changes may be made without departing from the scope of the invention.

Definitions

All numerical designations, such as pH, temperature, time, concentration, and molecular weight, including ranges, are approximations which are varied up or down by increments of 1.0 or 0.1, as appropriate. It is to be understood, even if it is not always explicitly stated that all numerical designations are preceded by the term "about". It is also to be understood, even if it is not always explicitly stated, that the reagents described herein are merely exemplary and that equivalents of such are known in the art and can be substituted for the reagents explicitly stated herein.

The term "about" or "approximately" as used herein refers to being within an acceptable error range for the particular value as determined by one of ordinary skill in the art, which will depend in part on how the value is measured or determined, i.e. the limitations of the measurement system, i.e. the degree of precision required for a particular purpose. As used herein, "about" refers to within ±10%.

Concentrations, amounts, solubilities, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include the individual values and sub-ranges within the indicated range, to the tenth of the unit. Thus, included in this numerical range are individual values such as 2, 3, and 4 and sub-ranges such as from 1-3, from 2-4 and from 3-5, etc. This same principle applies to ranges reciting only one numerical value. Furthermore, such an interpretation should apply regardless of the range or the characteristics being described.

"Subject" is used to describe an animal, preferably a mammal, more preferably a human, to whom treatment is administered, including prophylactic treatment with the compositions of the present invention. "Subject" and "patient" are used interchangeably herein.

The term "expression level" as used herein refers to detecting the amount or level of expression of a biomarker of the present invention. The act of actually detecting the expression level of a biomarker refers to the act of actively determining whether a biomarker is expressed in a sample or not. This act can include determining whether the biomarker expression is upregulated, downregulated or substantially unchanged as compared to a control level expressed in a sample. The expression level in some cases may refer to detecting transcription of the gene encoding a biomarker protein and/or to detecting translation of the biomarker protein.

Expression of genes/transcripts and/or polypeptides encoded by the genes represented by the biomarkers of the present invention can be measured by any of a variety of methods known in the art. In general, expression of a nucleic acid molecule (e.g. RNA or DNA) can be detected by any suitable method or technique of measuring or detecting gene or polynucleotide sequence or expression. Such methods include, but are not limited to, polymerase chain reaction (PCR), reverse transcriptase PCR (RT-PCR), in situ PCR, quantitative PCR (q-PCR), in situ hybridization, Southern blot, Northern blot, sequence analysis, microarray analysis, detection of a reporter gene, or any other DNA/RNA hybridization platforms.

The term "quantifying" or "quantitating" when used in the context of quantifying transcription levels of a gene can refer to absolute or relative quantification. Absolute quantification can be achieved by including known concentration(s) of one or more target nucleic acids and referencing the hybridization intensity of unknowns with the known target nucleic acids (e.g. through the generation of a standard curve). Alternatively, relative quantification can be achieved by comparison of hybridization signals between two or more genes, or between two or more treatments to quantify the changes in hybridization intensity and, by implication transcription level.

Methods to measure protein/polypeptide expression levels of selected biomarkers in the present invention include, but are not limited to: Western blot, immunoblot, enzyme-linked immunosorbent assay (ELISA), radioimmunoassay (MA), immunoprecipitation, surface plasmon resonance, chemiluminescence, fluorescent polarization, phosphorescence, immunohistochemical analysis, liquid chromatography mass spectrometry (LC-MS), matrix-assisted laser desorption/ionization time-of-flight (MALDI-TOF), mass spectrometry, microcytometry, microarray, microscopy, fluorescence activated cell sorting (FACS), flow cytometry, and assays based on a property of the protein including but not limited to DNA binding, ligand binding, or interaction with other protein partners.

The terms "diagnosing" or "diagnosis" as used herein refers to identification or classification of a molecular or pathological state, disease or condition (e.g., cancer). For example, "diagnosis" may refer to identification of a particular type of cancer. "Diagnosis" may also refer to the classification of a particular subtype of cancer, for instance, by histopathological criteria, or by molecular features (e.g., a subtype characterized by expression of one or a combination of biomarkers (e.g., particular genes or proteins encoded by said genes)).

The term "prognosis" refers to the determination or prediction of the course of disease or condition or to monitoring disease progression or regression from one biological state to another. Prognosis can include the determination of the time course of a disease, with or without treatment. Where treatment is included, the prognosis includes determining the efficacy of the treatment for the disease or condition.

The terms "risk or susceptibility" as used herein refers to the determination as to whether a subject would or would not respond to a particular therapy such as chemotherapy, such as one or more alkylating agents; radiotherapy; adjuvant therapy; surgery; or a combination thereof in order to optimize therapy for an individual subject. Cancers that express biomarkers that are indicative of a more highly aggressive cancer or poor prognosis may be treated with more aggressive therapies.

The term "treatment" or "treating" as used herein refers to the ability to ameliorate, suppress, mitigate, or eliminate the clinical symptoms after the onset of a disease state. Treatment can include chemicals, such as chemotherapeutic agents, immunotherapy agents or test compounds, and/or non-chemical treatment such as radiation, electrical pulses, and magnetic fields. An effective or successful treatment provides a clinically observable improvement.

"Sample," as used herein, refers to a composition that is obtained or derived from a subject and/or individual of interest that contains a cellular and/or other molecular entity that is to be characterized and/or identified, for example, based on physical, biochemical, chemical, and/or physiological characteristics. For example, the phrase "disease sample" and variations thereof refers to any sample obtained from a subject of interest that would be expected or is known to contain the cellular and/or molecular entity that is to be characterized. Samples include, but are not limited to, tissue samples, primary or cultured cells or cell lines, cell supernatants, cell lysates, platelets, serum, plasma, vitreous fluid, lymph fluid, synovial fluid, follicular fluid, seminal fluid, amniotic fluid, milk, whole blood, blood-derived cells, urine, cerebro-spinal fluid, saliva, sputum, tears, perspiration, mucus, tumor lysates, and tissue culture medium, tissue extracts such as homogenized tissue, tumor tissue, cellular extracts, and combinations thereof.

"Tissue sample" or "cell sample" is meant a collection of similar cells obtained from a tissue of a subject or individual. The source of the tissue or cell sample may be solid tissue as from a fresh, frozen and/or preserved organ, tissue sample, biopsy, and/or aspirate; blood or any blood constituents such as plasma; bodily fluids such as cerebral spinal fluid, amniotic fluid, peritoneal fluid, or interstitial fluid; cells from any time in gestation or development of the subject. The tissue sample may also be primary or cultured cells or cell lines. Optionally, the tissue or cell sample is obtained from a disease tissue/organ. For instance, a "tumor sample" is a tissue sample obtained from a tumor or other cancerous tissue. The tissue sample may contain a mixed population of cell types (e.g., tumor cells and non-tumor cells, cancerous cells and non-cancerous cells). The tissue sample may contain compounds which are not naturally intermixed with the tissue in nature such as preservatives, anticoagulants, buffers, fixatives, nutrients, antibiotics, or the like.

The term "biomarker" is used herein to refer to a molecule whose level of nucleic acid or protein product has a quantitatively differential concentration or level with respect to an aspect of a biological state of a subject. "Biomarker" is used interchangeably with "marker" herein. The level of the biomarker can be measured at both the nucleic acid level as well as the polypeptide level. At the nucleic acid level, a nucleic acid gene or a transcript which is transcribed from any part of the subject's chromosomal and extrachromosomal genome, including for example the mitochondrial genome, may be measured. Preferably an RNA transcript, more preferably an RNA transcript includes a primary transcript, a spliced transcript, an alternatively spliced transcript, or an mRNA of the biomarker is measured. At the polypeptide level, a pre-propeptide, a propeptide, a mature peptide or a secreted peptide of the biomarker may be measured. A biomarker can be used either solely or in conjunction with one or more other identified biomarkers so as to allow correlation to the biological state of interest as defined herein. Specific examples of biomarkers covered by the present invention include genes AQP4, ATP13A4, C4BPA, CAMK2N1, FMO2, FOXE1, GATA3, HOXA11, IRX2, LRRC4, NAPSA, PEBP4, RPL39L SCGB3A1, SCGB3A2, SFTA1P, SFTPA2, SFTPB, and SFTPD.

The term "biological state" as used herein refers to the result of the occurrence of a series of biological processes. As the biological processes change relative to each other, the biological state also changes. One measurement of a biological state is the level of activity of biological variables such as biomarkers, parameters, and/or processes at a specified time or under specified experimental or environmental conditions. A biological state can include, for example, the state of an individual cell, a tissue, an organ, and/or a multicellular organism. A biological state can be measured in samples taken from a normal subject or a diseased subject thus measuring the biological state at different time intervals may indicate the progression of a disease in a subject. The biological state may include a state that is indicative of disease (e.g. diagnosis); a state that is indicative of the progression or regression of the disease (e.g. prognosis); a state that is indicative of the susceptibility (risk) of a subject to therapy for the disease; and a state that is indicative of the efficacy of a treatment of the disease. The biological state may include normal cells or tissues, pre-cancerous cells or tissues, pre-invasive cells or tissues and invasive cells or tissue.

The term "cell" or "cells" is used synonymously herein and refers to in vitro cultures of mammalian cells grown and maintained as known in the art, as well as biological samples obtained from tumor specimens or normal specimens in vivo.

The term "baseline level" or "control level" of biomarker expression or activity refers to the level against which biomarker expression in the test sample can be compared. In some embodiments, the baseline level can be a normal level, meaning the level in a sample from a normal patient. This allows a determination based on the baseline level of biomarker expression or biological activity, whether a sample to be evaluated for disease cell growth has a measurable increase, decrease, or substantially no change in biomarker expression as compared to the baseline level. The term "negative control" used in reference to a baseline level of biomarker expression generally refers to a baseline level established in a sample from the subject or from a population of individuals which is believed to be normal (e.g. non-tumorous, not undergoing neoplastic transformation, not exhibiting inappropriate cell growth). In other embodiments, the baseline level can be indicative of a positive diagnosis of disease (e.g. positive control). The term "positive control" as used herein refers to a level of biomarker expression or biological activity established in a sample from a subject, from another individual, or from a population of individuals, where the sample was believed, based on data from that sample, to have the disease (e.g. tumorous, cancerous, exhibiting inappropriate cell growth). In other embodiments, the baseline level can be established from a previous sample from the subject being tested, so that the disease progression or regression of the subject can be monitored over time and/or the efficacy of treatment can be evaluated.

The term "neoplasia", "cancer", "tumor", "cancerous", and malignant" as used herein, refer to the physiological condition in mammals that is typically characterized by unregulated cell growth or the presence of tumors. The terms are used interchangeably herein. Examples of cancer benefited by the present invention include, but are not limited to, urothelial carcinoma including metastatic urothelial carcinoma and squamous cell carcinoma including head and neck or lung primaries.

The term "pre-cancerous" as used herein refers to a physiological condition in mammals that is typically associated with a significantly increased risk of cancer.

The term "pre-invasive" as used herein refers to a physiological condition in mammals that is typically associated with a localized tumor or cancer that has a risk of spreading to other tissues of the body.

The term "invasive" or "metastatic" as used herein refers to a physiological condition in mammals that is typically associated with cancer which has spread to multiple locations or tissues in the body.

The term "gene expression product" or "expression product" as used herein refers to an RNA transcribed from a gene (either pre- or post-processing) or an amino acid (e.g. a polypeptide, protein, or peptide regardless of any secondary modifications, such as glycosylation, lipidation or phosphorylation) encoded by the gene and generated by the gene when the gene is transcribed (either pre- or post-modification) and translated. An agent is said to increase gene expression if the application of a therapeutically effective amount of the agent to a cell or subject results in an increase in either an RNA or polypeptide expression product or both. An agent is said to decrease gene expression if the application of a therapeutically effective amount of the agent to a cell or subject results in a decrease in either an RNA or polypeptide expression product or both.

The term "polynucleotide" or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase, or by a synthetic reaction. Thus, for instance, polynucleotides as defined herein include, without limitation, single- and double-stranded DNA, DNA including single- and double-stranded regions, single- and double-stranded RNA, and RNA including single- and double-stranded regions, hybrid molecules comprising DNA and RNA that may be single-stranded or, more typically, double-stranded or include single- and double-stranded regions. In addition, the term "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. The term "polynucleotide" specifically includes cDNAs. The polynucleotide can include polymers having backbone modifications. It includes the recited sequences as well as their complementary sequences, which can be easily ascertained by those of ordinary skill in the art.

The term "polypeptide" as used herein refers to a compound made up of a single-chain of amino acid residues that are linked by peptide bonds. The term "protein" may be synonymous with the term "polypeptide" or may refer, in addition, to a complex of two or more polypeptides. Generally, polypeptides and proteins are formed predominantly of naturally occurring amino acids.

An "isolated polynucleotide" as used herein refers to a polynucleotide which is separated from other nucleic acid molecules which are present in the natural source of the polynucleotide. Preferably, an "isolated polynucleotide" is free of sequences which naturally flank the polynucleotide in the genomic DNA of the organism from which the nucleic acid is derived. An "isolated polynucleotide" is substantially free of other cellular material, gel materials, and culture medium when produced by recombinant techniques, or substantially free of chemical precursors or other chemicals when chemically synthesized. The polynucleotides of the present invention may be isolated from a variety of sources, such as PCR amplification from genomic DNA, mRNA, or cDNA libraries derived from the mRNA using standard techniques.

A "probe set" as used herein refers to a group of one or more polynucleotides that each selectively hybridize to the same target (for example, a specific genomic region or mRNA) that correlates with cancer diagnosis. As such, a single "probe set" may comprise any number of different isolated polynucleotides that selectively hybridize to a given target. A "probe" is a singular polynucleotide that selectively hybridizes to a target.

"Urothelial carcinoma gene expression signature" as used herein refers to the specific pattern of gene modulation of specific genes in neoplasias, specifically in urothelial carcinoma, particularly metastatic urothelial carcinoma in the lung, and squamous cell carcinoma of the head and neck or lung. The gene expression signature is comprised of the genes AQP4, ATP13A4, C4BPA, CAMK2N1, FMO2, FOXE1, GATA3, HOXA11, IRX2, LRRC4, NAPSA, PE 3P4, RPL39L, SCGB3A1, SCGB3A2, SFTA1P, SFTPA2, SFTPB, and SFTPD.

"Multiplex-PCR" as used herein refers to a single PCR reaction carried out on nucleic acid obtained from a single source (e.g., an individual) using more than one primer set for the purpose of amplifying two or more DNA sequences in a single reaction.

"Polymerase chain reaction" or "PCR" as used herein generally refers to a procedure wherein minute amounts of a specific piece of nucleic acid, RNA and/or DNA, are amplified as described, for example, in U.S. Pat. No. 4,683,195. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage, or plasmid sequences, etc. As used herein, PCR is considered to be one, but not the only, example of a nucleic acid polymerase reaction method for amplifying a nucleic acid test sample, comprising the use of a known nucleic acid (DNA or RNA) as a primer and utilizes a nucleic acid polymerase to amplify or generate a specific piece of nucleic acid or to amplify or generate a specific piece of nucleic acid which is complementary to a particular nucleic acid.

"Quantitative real-time polymerase chain reaction" or "qRT-PCR" as used herein refers to a form of PCR wherein the amount of PCR product is measured at each step in a PCR reaction.

"Microarray" as used herein refers to an ordered arrangement of hybridizable array elements, preferably polynucleotide probes, on a substrate.

"Administering" as used herein refers to a method of giving a dosage of a compound (e.g., an antagonist) or a pharmaceutical composition (e.g., a pharmaceutical composition including an antagonist) to a subject (e.g., a patient). Administering can be by any suitable means, including parenteral, intrapulmonary, and intranasal, and, if desired for local treatment, intralesional administration. Parenteral infusions include, for example, intramuscular, intravenous, intraarterial, intraperitoneal, or subcutaneous administration. Dosing can be by any suitable route, e.g., by injections, such as intravenous or subcutaneous injections, depending in part on whether the administration is brief or chronic. Various dosing schedules including but not limited to single or multiple administrations over various time-points, bolus administration, and pulse infusion are contemplated herein.

A "therapeutically effective amount" as used herein is defined as concentrations or amounts of components which are sufficient to effect beneficial or desired clinical results, including, but not limited to, inhibiting neoplastic transformation of cells; inhibiting inappropriate cell growth; inhibiting the proliferation of neoplastic/cancerous cells; inducing apoptosis in neoplastic/cancerous cells; and enhancing the therapeutic effect of chemotherapy medications. Compositions of the present invention can be used to effect a favorable change in the condition whether that change is an improvement or a complete elimination of symptoms due to neoplasia/cancer. In accordance with the present invention, a suitable single dose size is a dose that is capable of preventing or alleviating (reducing or eliminating) a symptom in a subject when administered one or more times over a suitable time period. One of skill in the art can readily determine appropriate single dose sizes for systemic administration based on the size of the animal and the route of administration. The therapeutically effective amount of the compositions of the present invention encompasses providing cancer treatment or enhancing cancer treatment without causing significant side effects or adverse reactions.

"Chemotherapy" or "chemotherapeutic agent" as used herein refers to a chemical compound useful in the treatment of cancer. Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL@); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB 1-TM1); eleutherobin; pancratistatin; a sarcodictyin; spongistatin; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, especially calicheamicin γ1I and calicheamicin ω1I (see, e.g., Nicolaou et al., *Angew. Chem Intl. Ed. Engl.,* 33: 183-186 (1994)); dynemicin, including dynemicin A; an esperamicin; as well as neocarzinostatin chromophore and related chromoprotein enediyne antiobiotic chromophores, aclacinomysins, actinomycin, authramycin, azaserine, bleomycins, cactinomycin, carabicin, carminomycin, carzinophilin, chromomycin, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products. Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE@, FILDESIN®); dacarbazine; mannomustine; mitobronitol; mitolactol; pipobroman; gacytosine; arabinoside ("Ara-C"); thiotepa; taxoids, for example taxanes including TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® docetaxel (Rhne-Poulenc Rorer, Antony, France); chloranbucil; gemcitabine (GEMZAR®); 6-thioguanine; mercaptopurine; methotrexate; platinum or platinum-based chemotherapy agents and platinum analogs, such as cisplatin, carboplatin, oxaliplatin (ELOXATIN™), satraplatin, picoplatin, nedaplatin, triplatin, and lipoplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluorometlhylornithine (DMFO); retinoids such as retinoic acid; capecitabine (XELODA®); pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovorin. Additional chemotherapeutic agents include the cytotoxic agents useful as antibody drug conjugates, such as maytansinoids (DM1, for example) and the auristatins MMAE and MMAF, for example.

"Chemotherapeutic agents" also include "anti-hormonal agents" or "endocrine therapeutics" that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), EVISTA® raloxifene, droloxifene, 4-hydroxytamoxifen, trioxifene, keoxifene, LY117018, onapristone, and FARES TON® toremifene; anti-progesterones; estrogen receptor down-regulators (ERDs); agents that function to suppress or shut down the ovaries, for example, leutinizing hormone-releasing hormone (LHRH) agonists such as LUPRON® and ELIGARD® leuprolide acetate, goserelin acetate, buserelin acetate and tripterelin; other anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide. MEGASE® megestrol acetate, AROMASIN® exemestane, formestanie, fadrozole, RIVISOR® vorozole, FEMARA® letrozole, and ARIMIDEX® anastrozole. In addition, such definition of chemotherapeutic agents includes bisphosphonates such as clodronate (for example, BONEFOS® or OSTAC®), DIDROCAL@etidronate, NE-58095, ZOMETA® zoledronic acid/zoledronate, FOSAMAX® alendronate, AREDIA® pamidronate, SKELID® tiludronate, or ACTONEL® risedronate; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGFR); vaccines such as THERATOPE® vaccine and gene therapy vaccines, for example, ALLOVECTIN® vaccine, LEUVECTIN® vaccine, and VAXID® vaccine; LURTOTECAN® topoisomerase 1 inhibitor, ABARELIX® mRH; lapatinib ditosylate (an ErbB-2 and EGFR dual tyrosine kinase small-molecule inhibitor also known as GW572016): and pharmaceutically acceptable salts, acids or derivatives of any of the above.

Chemotherapeutic agents also include antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG®, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth). Additional humanized monoclonal antibodies with therapeutic potential as agents in combination with the compounds of the invention include: apolizumab, aselizumab, atlizumab, bapineuzumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, tucotuzumab celmoleukin, tucusituzumab, umavizumab, urtoxazumab, ustekinumab, visilizumab, and the anti-interleukin-12 (ABT-874/J695, Wyeth Research and Abbott Laboratories) which is a recombinant exclusively human-sequence, full-length IgG1λ antibody genetically modified to recognize interleukin-12 p40 protein.

Chemotherapeutic agents also include "EGFR inhibitors," which refers to compounds that bind to or otherwise interact directly with EGFR and prevent or reduce its signaling activity, and is alternatively referred to as an "EGFR antagonist." Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBUTIX®) and reshaped human 225 (H225) (see, WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF or Panitumumab (see WO98/50433, Abgenix/Amgen); EMD 55900 (Stragliotto et al. *Eur. J. Cancer* 32A:636-640 (1996)); EMD7200 (matuzumab) a humanized EGFR antibody directed against EGFR that competes with both EGF and TGF-alpha for EGFR binding (EMD/Merck); human EGFR antibody, HuMax-EGFR (GenMab); fully human antibodies known as E1.1, E2.4, E2.5, E6.2, E6.4, E2.11, E6.3, and E7.6. 3 and described in U.S. Pat. No. 6,235,883; MDX-447 (Medarex Inc); and mAb 806 or humanized mAb 806 (Johns et al., *J. Biol. Chem.* 279(29): 30375-30384 (2004)). The anti-EGFR antibody may be conjugated with a cytotoxic agent, thus generating an immunoconjugate (see, e.g., EP 659,439A2, Merck Patent GmbH). EGFR antagonists include small molecules such as compounds described in U.S. Pat. Nos. 5,616,582, 5,457, 105, 5,475,001, 5,654,307, 5,679.683, 6,084,095, 6,265,410, 6,455,534, 6,521,620, 6,596,726, 6,713,484, 5,770,599, 6,140,332, 5,866,572, 6,399,602, 6,344,459, 6,602,863, 6,391,874, 6,344,455, 5,760,041, 6,002,008, and 5,747,498, as well as the following PCT publications: WO 98/14451, WO 98/50038, WO 99/09016, and WO 99/24037. Particular small molecule EGFR antagonists include OSI-774 (CP-358774, erlotinib, TARCEVA® Genentech/OSI Pharmaceuticals); PD 183805 (Cl 1033, 2-propenamide, N44-[(3-chloro-4-fluorophenyl)amino]-7-[3-(4-morpholinyl) propoxy]-6-quinazolinyl]-, dihydrochloride, Pfizer Inc.); ZD1839, gefitinib (IRESSA®) 4-(3'-Chloro-4'-fluoroanilino)-7-methoxy-6-(3-morpholinopropoxy)quinazoline, AstraZeneca); ZM 105180 ((6-amino-4-(3-methylphenyl-amino)-quinazoline, Zeneca); BIBX-1382 (N8-(3-chloro-4-fluoro-phenyl)-N2-(1-methyl-piperidin-4-yl)-pyrimido[5,4-d]pyrimidine-2,8-diamine, Boehringer Ingelheim); PKI-166 ((R)-4-[4-[(1-phenylethyl)amino]-1H-pyrrolo[2,3-d]pyrimidin-6-yl]-phenol); (R)-6-(4-hydroxyphenyl)-4-[(1-phenylethyl)amino]-7H-pyrrolo[2,3-d]pyrimidine); CL-387785 (N-[4-[(3-bromophenyl)amino]-6-quinazolinyl]-2-butynamide); EKB-569 (N44-[(3-chloro-4-fluorophenyl)amino]-3-cyano-7-ethoxy-6-quinolinyl]-4-(dimethylamino)-2-butenamide) (Wyeth); AG1478 (Pfizer); AG1571 (SU 5271; Pfizer); and dual EGFR/HER2 tyrosine kinase inhibitors such as lapatinib (TYKERB®, GSK572016 or N-[3-chloro-4-[(3 fluorophenyl)methoxy]phenyl]-6 [5 [[[2methylsulfonyl)ethyl]amino]methyl]-2-furanyl]-4-quinazolinamine).

Chemotherapeutic agents also include "tyrosine kinase inhibitors" including the EGFR-targeted drugs noted in the preceding paragraph; small molecule HER2 tyrosine kinase inhibitors such as TAK165 available from Takeda; CP-724, 714, an oral selective inhibitor of the ErbB2 receptor tyrosine kinase (Pfizer and OSI); dual-HER inhibitors such as EKB-569 (available from Wyeth) which preferentially binds EGFR but inhibits both HER2 and EGFR-overexpressing cells; lapatinib (GSK572016; available from Glaxo-SmithKline), an oral HER2 and EGFR tyrosine kinase inhibitor; PKI-166 (available from Novartis); pan-HER inhibitors such as canertinib (C1-1033; Pharmacia); Raf-1 inhibitors such as antisense agent ISIS-5132 available from ISIS Pharmaceuticals which inhibit Raf-1 signaling; non-HER targeted TK inhibitors such as imatinib mesylate (GLEEVEC®, available from Glaxo SmithKline); multi-targeted tyrosine kinase inhibitors such as sunitinib (SUTENT®, available from Pfizer); VEGF receptor tyrosine kinase inhibitors such as vatalanib (PTK787/ZK222584, available from Novartis/Schering AG); MAPK extracellular regulated kinase I inhibitor C1-1040 (available from Pharmacia); quinazolines, such as PD 153035,4-(3-chloroanilino) quinazoline; pyridopyrimidines; pyrimidopyrimidines; pyrrolopyrimidines, such as CGP 59326, CGP 60261 and CGP 62706; pyrazolopyrimidines, 4-(phenylamino)-7H-pyrrolo[2,3-d] pyrimidines; curcumin (diferuloyl methane, 4,5-bis (4-fluoroanilino)phthalimide); tyrphostines containing nitrothiophene moieties: PD-0183805 (Warner-Lamber); antisense molecules (e.g., those that bind to HER-encoding nucleic acid): quinoxalines (U.S. Pat. No. 5,804, 396); tryphostins (U.S. Pat. No. 5,804,396); ZD6474 (Astra Zeneca); PTK-787 (Novartis/Schering AG); pan-HER inhibitors such as C1-1033 (Pfizer); Affinitac (ISIS 3521; Isis/Lilly); imatinib mesylate (GLEEVEC®); PKI 166 (Novartis); GW2016 (Glaxo SmithKline); C1-1033 (Pfizer); EKB-569 (Wyeth); Semaxinib (Pfizer); ZD6474 (AstraZeneca); PTK-787 (Novartis/Schering AG); INC-1C11 (Imclone), rapamycin (sirolimus, RAPAMUNE®); or as described in any of the following patent publications: U.S. Pat. No. 5,804,396; WO 1999/09016 (American Cyanamid); WO 1998/43960 (American Cyanamid); WO 1997/38983 (Warner Lambert); WO 1999/06378 (Warner Lambert); WO 1999/06396 (Warner Lambert); WO 1996/30347 (Pfizer, Inc); WO 1996/33978 (Zeneca); WO 1996/3397 (Zeneca) and WO 1996/33980 (Zeneca).

Chemotherapeutic agents also include dexamethasone, interferons, colchicine, metoprine, cyclosporine, amphotericin, metronidazole, alemtuzumab, alitretinoin, allopurinol, amifostine, arsenic trioxide, asparaginase, BCG live, bevacuzimab, bexarotene, cladribine, clofarabine, darbepoetin alfa, denileukin, dexrazoxane, epoetin alfa, elotinib, filgrastim, histrelin acetate, ibritumomab, interferon alfa-2a, interferon alfa-2b, lenalidomide, levamisole, mesna, methoxsalen, nandrolone, nelarabine, nofetumomab, oprelvekin, palifermin, pamidronate, pegademase, pegaspargase, pegfilgrastim, pemetrexed disodium, plicamycin, porfimer sodium, quinacrine, rasburicase, sargramostim, temozolomide, VM-26, 6-TG, toremifene, tretinoin, ATRA, valrubicin, zoledronate, and zoledronic acid, and pharmaceutically acceptable salts thereof.

Chemotherapeutic agents also include hydrocortisone, hydrocortisone acetate, cortisone acetate, tixocortol pivalate, triamcinolone acetonide, triamcinolone alcohol, mometasone, amcinonide, budesonide, desonide, fluocinonide, fluocinolone acetonide, betamethasone, betamethasone sodium phosphate, dexamethasone, dexamethasone sodium phosphate, fluocortolone, hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate and fluprednidene acetate; immune selective anti-inflammatory peptides (ImSAIDs) such as phenylalanine-glutamine-glycine (FEG) and its D-isomeric form (feG) (IMULAN BioTherapeutics, LLC); anti-rheumatic drugs such as azathioprine, ciclosporin (cyclosporine A), D-penicillamine, gold salts, hydroxychloroquine, leflunomideminocycline, sulfasalazine, tumor necrosis factor alpha (TNFα) blockers such as etanercept (ENBREL®), infliximab (REMICADE®), adalimumab (HUMIRA®), certolizumab pegol (CIMZIA®), golimumab (SIMPONI®), Interleukin 1 (IL-1) blockers such as anakinra (KINERET®), T-cell co-stimulation blockers such as abatacept (ORENCIA®), Interleukin 6 (IL-6) blockers such as tocilizumab (ACTEMERA®); Interleukin 13 (IL-13) blockers such as lebrikizumab; Interferon alpha (IFN) blockers such as rontalizumab; beta 7 integrin blockers such as rhuMAb Beta7; IgE pathway blockers such as Anti-M1 prime: Secreted homotrimeric LTa3 and membrane bound heterotrimer LTa1/β2 blockers such as Anti-lymphotoxin alpha (LTa); miscellaneous investigational agents such as thioplatin, PS-341, phenylbutyrate, ET-18-OCH3, and famesyl transferase inhibitors (L-739749, L-744832); polyphenols such as quercetin, resveratrol, piceatannol, epigallocatechine gallate, theaflavins, flavanols, procyanidins, betulinic acid and derivatives thereof; autophagy inhibitors such as chloroquine: delta-9-tetrahydrocannabinol (dronabinol, MARINOL®): beta-lapachone; lapachol; colchicines: betulinic acid; acetylcamptothecin, scopolectin, and 9-aminocamptothecin); podophyllotoxin; tegafur (UFTORAL®); bexarotene (TARGRETIN®);

bisphosphonates such as clodronate (for example, BONEFOS® or OSTAC®), etidronate (DIDROCAL®), NE-58095, zoledronic acid/zoledronate (ZOMETA@), alendronate (FOSAMAX®), pamidronate (AREDIA®), tiludronate (SKELID®), or risedronate (ACTONEL®); and epidermal growth factor receptor (EGF-R); vaccines such as THERATOPE® vaccine; perifosine, COX-2 inhibitor (e.g., celecoxib or etoricoxib), proteosome inhibitor (e.g., PS341); CC1-779; tipifarnib (R11577); orafenib, ABT510; Bcl-2 inhibitor such as oblimersen sodium (GENASENSE®); pixantrone; farnesyltransferase inhibitors such as lonafamib (SCH 6636, SARASAR™); and pharmaceutically acceptable salts, acids or derivatives of any of the above; as well as combinations of two or more of the above.

"Immunotherapy" as used herein refers to a biologic therapy cancer treatment that boosts the body's natural defenses to fight cancer using substances produced in the body, or made in a lab, to improve or restore immune function. Immunotherapies include, but are not limited to, monoclonal antibodies such as naked, conjugated and bispecific; immune checkpoint inhibitors such as programmed death 1 (PD-1) or programmed death-ligand (PD-L1) inhibitors, cytotoxic T-lymphocyte-associated antigen (CTLA-4) inhibitors; non-specific immunotherapies (cytokines) such as interferons, interleukins and colony stimulating factors; oncolytic virus therapy; T-cell therapy such as adoptive cell transfer (ACT) therapies including, but not limited to, chimeric antigen receptor (CAR) T-cell therapy, T-cell receptor (TCR) therapy, and tumor-infiltrating lymphocytes (TIL) therapy; cancer vaccines; immune modulators such as drugs targeting immune proteins CD137.4-1BB, CD27, GITR and OX40; adjuvant immunotherapies such as toll-like receptors (TLRs). *Bacillus* Calmette-Guerin (BCG), granulocyte macrophage colony-stimulating factor (GM-CSF). In some embodiments, combinations of two or more of the above may be used.

Urothelial carcinoma (UC) can mimic a squamous cell carcinoma (SCC) and it may be difficult to distinguish the two especially in metastatic sites. The two cancers have an overlapping immunohistochemical profile (both positive for CK5/6, CK7, p63 and p40), making immunohistochemical diagnosis difficult. GATA3, although relatively specific for UC, can be expressed in SCC. Existing GATA3 staining methods only allow for limited distinction with a success rate of only 80% or less due to GATA3 expression being reduced in UC metastatic lesions and up to 20% of lung primary SCC expressing GATA3. It is important to distinguish the two cancers for proper patient management. In cases of metastases from unknown primary, it is important to know if it is urothelial carcinoma or SCC and if possible the primary site of origin so that the patient gets the best treatment Currently IHC in combination with clinical assessment is used to make a best guess as to the origin of the tumor. A common scenario is a patient with a lung lesion and coexistent urothelial lesion. GATA3 stain can help suggest urothelial origin as about 80 percent of UC express this marker. However, expression is reduced in metastatic lesions. Generally primary lung tumors don't express the marker, however some studies show up to 20% of lung tumors may express GATA3 and less than 80% of UC may express it decreasing its value. Further, it's very hard to distinguish the origin of squamous cancer between primary lung vs head and neck or elsewhere. This further classification of squamous cell cancer is also important to assign correct stage and to select appropriate therapy.

Previous studies have shown that gene expression profiling can be a helpful tool for cancer diagnosis. Micro-array based gene expression profiling has shown highly reproducible results, which along with the use of standardized protocols and array platforms has resulted in significant advances in gene annotation, simultaneously measure the expression of multiple markers.

Materials and Methods

A total of 161 UC cases and 38 head and neck (H&N) SCC cases and 268 lung SCC cases from Moffitt Cancer Center (MCC) Total Cancer Care (TCC) database were used as the training dataset. The gene expression data was derived from HuRSTA chips (Merck HuRSTA-2a520709 chips), each with 60607 probe sets for 26356 unique genes. Background correction, normalization, and summarizing of raw microarray data were performed using Robust Multi-Array Average (RMA) algorithm implemented in Bioconductor extensions to the R statistical programming environment.

Unpaired t-tests were performed on every gene to identify significantly differentially expressed genes for UC vs. SCC from lung vs. head-and-neck SCC. The top 19 most differentially expressed genes were selected for PCA (Principal Component Analysis) analysis, a linear transformation of the variables into a lower dimensional space which retains maximal amount of information about the variables. The differential expression of the top 19 genes is depicted in FIG. 6.

Tissue samples may be stored by a variety of methods including, but not limited to, fresh frozen, PFA and paraffin embedded.

While the gene expression data was performed on HuRSTA chips, other methods are available including, but not limited to, multiplex PCR such as qPCR (used for quantification of nucleic acids); Affymetrix (used for microarray); and nanostring (used for gene expression assay).

Suitable data analysis algorithms are known in the art such as Robust Multi-Array Average (RMA) algorithm, Classification and Regression Tree (CART), Multiple Additive Regression Tree (MART), Prediction Analysis for Microarrays (PAM), or Random Forest analysis. Such algorithms classify complex spectra from biological materials to distinguish subjects as normal or as possessing biomarker levels characteristic of a particular disease state. In other embodiments, a data analysis algorithm of the disclosure comprises ANOVA and nonparametric equivalents, linear discriminant analysis, logistic regression analysis, nearest neighbor classifier analysis, neural networks, principal component analysis, quadratic discriminant analysis, regression classifiers and support vector machines. While such algorithms may be used to construct an analytical process and/or increase the speed and efficiency of the application of the analytical process and to avoid investigator bias, one of ordinary skill in the art will realize that computer-based algorithms are not required to carry out the methods of the present disclosure.

As will be appreciated by those of skill in the art, a number of quantitative criteria can be used to communicate the performance of the comparisons made between a test marker profile and reference marker profiles. These include area under the curve (AUC), hazard ratio (HR), relative risk (RR), reclassification, positive predictive value (PPV), negative predictive value (NPV), accuracy, sensitivity and specificity, Net reclassification Index, Clinical Net Reclassification Index. In addition, other constructs such a receiver operator curves (ROC) can be used to evaluate analytical process performance.

Principal Component Analysis (PCA)

The first and second principal components (PC1 and PC2) of the 19 genes were used as the signature. PCA is mathematically defined as an orthogonal linear transformation that transforms the data to a new coordinate such that the greatest variance by some projection of the data comes to lie on the first coordinate (called the first principal component), the second greatest variance on the second coordinate, and so on. Consider a data matrix X, with column-wise zero empirical mean (the sample mean of each column has been shifted to zero), where each of the n rows represents a different sample, and each of the p columns represents a gene. Mathematically, the transformation is defined by a set of p-dimensional vectors of weights or loadings $w_{(k)}=(w_1, w_p)_{(k)}$ that map each row vector $x_i$ of X to a new vector of principal component scores $t_{(i)}=(t_1, \ldots, t_m)_{(i)}$, given by $t_{k(i)}=x_{(i)}\cdot w_{(k)}$ for $i=1, \ldots, n$ $k=1, \ldots, m$ in such a way that the individual variables of t considered over the data set successively inherit the maximum possible variance from x, with each loading vector w constrained to be a unit vector.

First Component

The first principal component of a data vector $x_{(i)}$ can be given as a score $t_{1(i)}=x_{(i)}\cdot w_{(1)}$ in the transformed co-ordinates, where the first loading vector $w_{(1)}$ has to satisfy $$w_{(1)} = \arg\max\left\{\frac{w^T X^T X w}{w^T w}\right\}$$

Further Components

The kth component can be found by subtracting the first k−1 principal components from X:

$$\hat{X}_k = X - \sum_{s=1}^{k-1} X w_{(s)} w_{(s)}^T$$

and then finding the loading vector which extracts the maximum variance from this new data matrix $$w_{(k)} = \underset{\|w\|=1}{\operatorname{argmax}}\left\{\|\hat{X}_k w\|^2\right\} = \arg\max\left\{\frac{w^T \hat{X}_k^T \hat{X}_k w}{w^T w}\right\}$$

The cutoffs of the first and second principal components were selected to maximize the total performance of the signature, i.e., max (sensitivity+specificity), for the training datasets. The cutoff for urothelial cancer was set at PC1<−5.1036 & PC2<2.1476.

The 19-gene signature was first self-validated on the training dataset with 157 out of 161 UCs correctly identified as UC and 302 out of 306 SCCs correctly identified as SCC (sensitivity=97.52%; specificity=98.69%).

The signature was further validated on external datasets publicly available at GEO datasets, with 96 cases of H&N SCC from GSE31056, 18 lung SCCs from GSE10245 and 93 UC from GSE31684, total of 207 cases. To validate the 19-gene signature on external datasets, the inventors first extracted the expression data of the 19 genes from each of the external datasets and centered the gene expressions by the means of the training dataset. Then the inventors calculated the first principal component scores (PC1s) and second principal component scores (PC2s) by applying the following formula:

$t_{k(i)}=x_{(i)}\cdot w_{(k)}$ for $i=1, \ldots, n$ $k=1,m$ where $x_{(i)}$ is a vector of expression values for $gene_{(i)}$ of the validation dataset and w(k) is a vector of loadings for $gene_{(i)}$ from the training dataset. Finally, the cutoffs obtained from the training dataset were applied to the PC scores of PC1s and PC2s of the validation dataset to classify each sample into UC or SCC.

From the training dataset, the signature correctly identified 157 of 161 UCs as UC and 302 of 306 SCCs as SCC (sensitivity=97.52%; specificity=98.69%). The ROC for the 19-gene signature on the Training datasets had an AUC=0.9848.

The signature was further validated on external datasets (validation dataset) publicly available at the GEO databases, with 96 cases of H&N SCC from GSE31056, 18 lung SCCs from GSE10245 and 93 UC from GSE31684, total of 207 cases.

The signature correctly identified all 112 of the publicly available SCCs with gene data (96 H&N and 16 lung) as SCC and all of 93 publicly available UCs with gene data (sensitivity=100%; specificity=98.24%) as UC. The ROC for the 19-gene signature on the Validation datasets had an AUC=0.9903 (PPV=98% and NPV=100%).

Hence, with PC1 cutoffs <−5.1036 and PC2<2.147621, the inventors could correctly classify 250 of 254 UCs and 414 of 420 H&N and lung SCCs.

Prophetic Example 1

A biopsy is taken from a lung tumor of a male patient who has urothelial carcinoma. Gene expression analysis is conducted on the biopsy sample using multiplex PCR for the genes comprising the 19-gene signature, namely genes AQP4, ATP13A4, C4BPA, CAMK2N1, FMO2, FOXE1, GATA3, HOXA11, IRX2, LRRC4, NAPSA, PEBP4, RPL39L, SCGB3A1, SCGB3A2, SFTA1P SFTPA2, SFTPB, and SFTPD. Principal component analysis is then used to determine the first principal component (PC1) and the second principal component (PC2). PC1 is <−5.1036 and PC2 is <2.147621 thus a diagnosis of metastatic urothelial carcinoma is made for the lung tumor biopsy and systemic treatment such as chemotherapy or immunotherapy is recommended.

Prophetic Example 2

A biopsy is taken from a lung tumor of a female patient. Gene expression analysis is conducted on the biopsy sample using multiplex PCR for the genes comprising the 19-gene signature, namely genes AQP4, ATP13A4, C4BPA, CAMK2N1, FMO2, FOXE1, GATA3, HOXA11, IRX2. LRRC4, NAPSA, PEBP4, RPL39L, SCGB3A1 SCGB3A2, SFTA1P, SFTPA2, SFTPB, and SFTPD. Principal component analysis is then used to determine the first principal component (PC1) and the second principal component (PC2). PC1 is >−5.1036 and PC2 is >2.147621 thus a diagnosis of squamous cell carcinoma is made for the lung tumor biopsy and surgery is recommended to remove the tumor.

Conclusion

The inventors have developed a way of identifying those patients having urothelial carcinoma from squamous cell carcinoma of the H&N and Lung primaries using a 19-gene signature. This 19-Gene expression profile can assist in distinguishing UCs from SCCs of H&N and lung primaries. This will make a significant impact on patient management and outcome.

The disclosures of all publications cited above are expressly incorporated herein by reference, each in its entirety, to the same extent as if each were incorporated by reference individually.

It is also to be understood that the following claims are intended to cover all of the generic and specific features of the invention herein described, and all statements of the scope of the invention which, as a matter of language, might be said to fall there between. Now that the invention has been described,

What is claimed is:

1. A method of diagnosing between urothelial carcinoma (UC) and squamous cell carcinoma (SCC) in a patient and treating the patient according to the diagnosis comprising:

obtaining or having obtained a tumor sample from the patient;

obtaining or having obtained expression levels of two or more genes in the tumor sample selected from the group consisting of AQP4, ATP13A4, C4BPA, CAMK2N1, FMO2, FOXE1, GATA3, HOXA11, IRX2, LRRC4, NAPSA, PEBP4, RPL39L, SCGB3A1, SCGB3A2, SFTA1P, SFTPA2, SFTPB, and SFTPD;

performing or having performed Principal Component Analysis (PCA) on the expression levels of the at least two or more genes to obtain a first Principal Component Analysis score (PCA1) and a second Principal Component Analysis score (PCA2);

wherein a diagnosis of UC is given if the PCA1 is below a first calculated cutoff and the PCA2 is below a second calculated cutoff;

wherein a diagnosis of SCC is given if the PCA1 is above or equal to the first calculated cutoff and the PCA2 is above or equal to the second calculated cutoff; and treating the patient using surgery if the diagnosis is SCC or treating the patient by administering chemotherapy or immunotherapy if the diagnosis is UC;

wherein the SCC is a carcinoma of head and neck or lung primaries.

2. The method of claim 1, wherein the first calculated cutoff for the PCA1 −5.1036 and the second calculated cutoff for PCA2 is 2.147621.

3. The method of claim 1, wherein the tumor sample is taken from a lung nodule of the patient.

4. The method of claim 1, wherein the tumor sample is taken from a metastatic site where a primary site is unknown.

5. The method of claim 1, wherein the patient currently has or previously had urothelial carcinoma.

6. The method of claim 1, wherein the UC is metastatic.

7. The method of claim 1, wherein the chemotherapy is a therapeutically effective amount of a platinum-based chemotherapeutic agent.

8. The method of claim 1, wherein the expression levels of the two or more genes are measured using multiplex PCR.

9. The method of claim 1, wherein the expression levels of all the genes AQP4, ATP13A4, C4BPA, CAMK2N1, FMO2, FOXE1, GATA3, HOXA11, IRX2, LRRC4, NAPSA, PEBP4, RPL39L, SCGB3A1, SCGB3A2, SFTA1P, SFTPA2, SFTPB, and SFTPD are determined.

10. The method of claim 9, wherein the expression levels of the genes are measured on HuRSTA chips.

* * * * *